US00PP33242P3

(12) United States Plant Patent
Bartley

(10) Patent No.: US PP33,242 P3
(45) Date of Patent: Jul. 6, 2021

(54) ***ANIGOZANTHOS* PLANT NAMED 'RAMBOPRISE'**

(50) Latin Name: ***Anigozanthos* hybrid**
Varietal Denomination: Ramboprise

(71) Applicant: Ramm Botanicals Pty. Ltd., Kangy Angy (AU)

(72) Inventor: Megan Bartley, Kangy Angy (AU)

(73) Assignee: Ramm Botanicals PTY, LTD.

( * ) Notice: Subject to any disclaimer, the term of this patent is extended or adjusted under 35 U.S.C. 154(b) by 0 days.

(21) Appl. No.: 16/898,808

(22) Filed: Jun. 11, 2020

(65) Prior Publication Data

US 2020/0404826 P1 Dec. 24, 2020

(51) Int. Cl.
*A01H 5/02* (2018.01)
*A01H 6/00* (2018.01)
*A01H 6/46* (2018.01)

(52) U.S. Cl.
USPC ..... Plt./362
CPC ..... *A01H 6/46* (2018.05)

(58) Field of Classification Search
USPC ..... Plt./263.1, 362
See application file for complete search history.

(56) References Cited

PUBLICATIONS

Australian Plants online: Paws for Reflection. 2000. h.ttp://anpsa.org.au/APOL17/mar00-5.html. Accessed Nov. 23, 2020. 4 pgs. (Year: 2000).*
UPOV-PLUTO: Plant Variety Database, Nov. 4, 2020, citation for 'Ramboprise'. (Year: 2020).*
Vaughan's Australian Plants. 2019. https://apsyarrayarra.files.wordpress.com/2019/08/phil-vaughan-stall-grafted-and-non-grafted.pdf. Accessed Nov. 23, 2020. 14 pgs. (Year: 2019).*

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Anigozanthos* plant named 'Ramboprise' is disclosed, characterized by a distinctive short plant height and orange flowers. Plants produce inflorescence having primary ramification. The new variety is a *Anigozanthos*, typically produced as a garden or container plant.

2 Drawing Sheets

Latin name of the genus and species: *Anigozanthos* hybrid.

Variety denomination: 'Ramboprise'.

BACKGROUND OF THE INVENTION

The new cultivar is a product of a planned breeding program. The new variety originated as the result of the crossing made during July 2013 of the female parent, an unpatented, proprietary *Anigozanthos* referred to as 'A02-0048' and the pollen parent, an unpatented *Anigozanthos* referred to as 'Bush Revelry'. 'Ramboprise' was discovered and selected by the inventor at a research greenhouse in New South Wales, Australia November of 2015.

Asexual reproduction of the new cultivar 'Ramboprise' was New South Wales, Australia at a research laboratory by tissue culture during 2015. 'Ramboprise' has since produced several generations and has shown that the unique features of this cultivar are stable and reproduced true to type.

SUMMARY OF THE INVENTION

The cultivar 'Ramboprise' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Ramboprise'. These characteristics in combination distinguish 'Ramboprise' as a new and distinct *Anigozanthos* cultivar:

1. Short plant habit.
2. Primary inflorescence ramification.
3. Orange flower color.

PARENTAL COMPARISON

Plants of the new cultivar 'Ramboprise' are comparable to the seed parent in most horticultural characteristics; however, the new variety 'Ramboprise' differs in the following:

1. The new variety produces primary inflorescence ramification, the seed parent does not produce inflorescence ramification.

Plants of the new cultivar 'Ramboprise' are comparable to the pollen parent in most horticultural characteristics; however, the new variety 'Ramboprise' differs in the following:

1. The new variety produces orange flowers, the pollen parent produces yellow flowers.

COMMERCIAL COMPARISON

Plants of the new cultivar 'Ramboprise' are comparable to the commercial *Anigozanthos* variety 'Rambofling', U.S. Plant Pat. No. 25,267. The two *Anigozanthos* varieties are similar in most horticultural characteristics; however, the new variety 'Ramboprise' differs in the following:

1. The new variety begins flowering earlier than this comparator.
2. Foliage of the new variety is brighter green than foliage of this comparator.

BRIEF DESCRIPTION OF THE PHOTOGRAPHS

Figure 1:
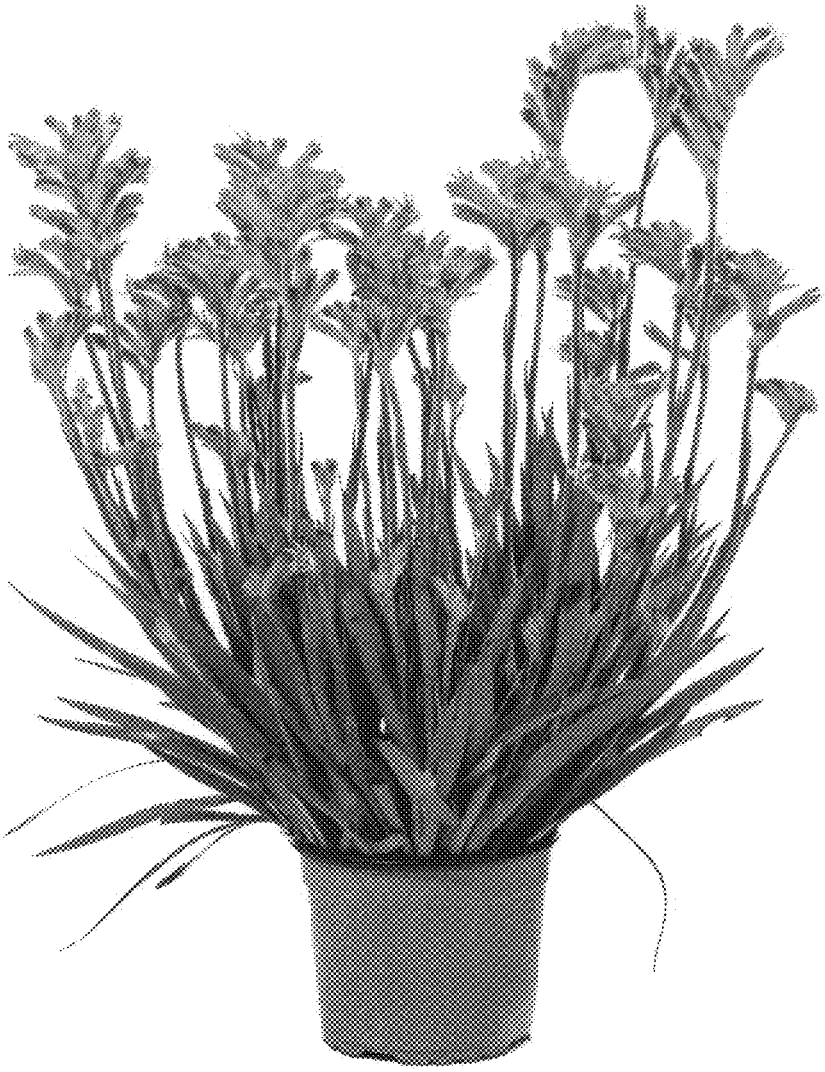

The accompanying photograph in FIG. 1 illustrates in full color a typical plant of 'Ramboprise' grown outdoors in Santa Paula, Calif. This plant is approximately 20 weeks old, shown in a 1 gallon pot.

Figure 2:
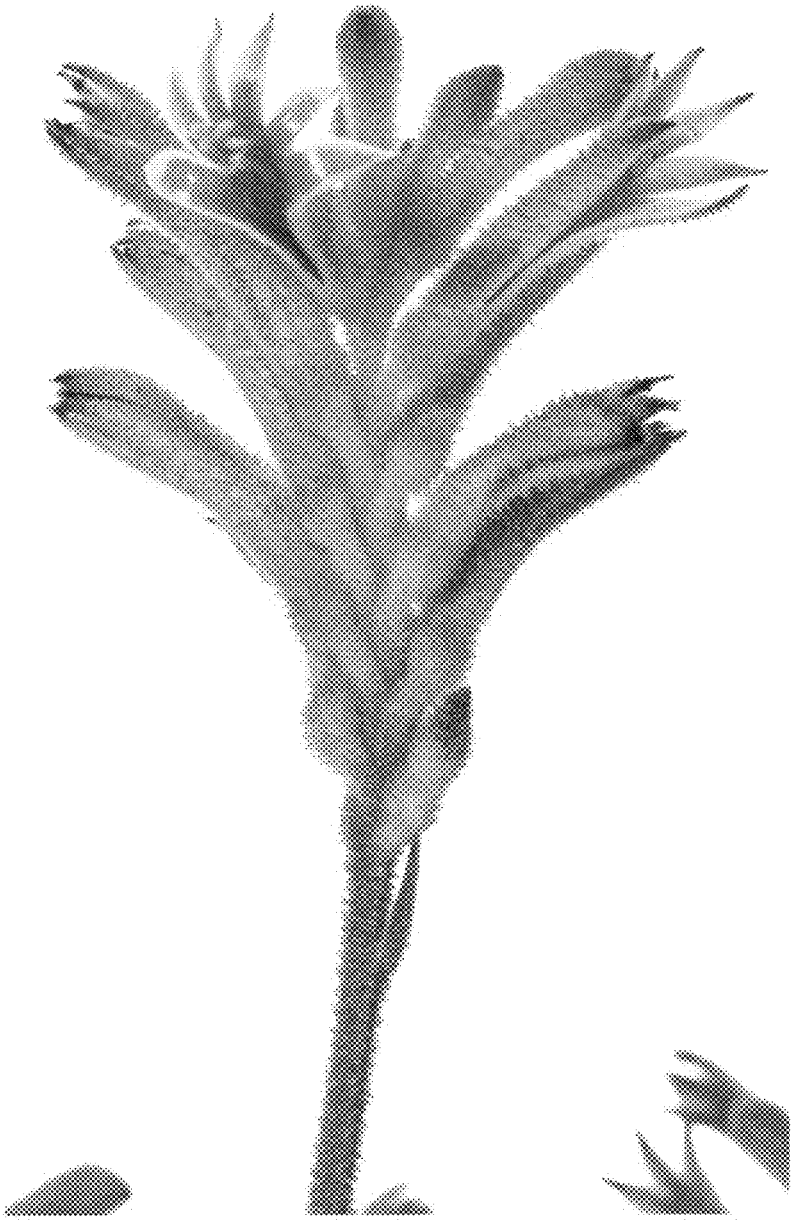

FIG. 2 illustrates a close-up view of the flowers.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'Ramboprise' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Anigozanthos* hybrid 'Ramboprise'.

PROPAGATION

Typically propagated by micropropagation tissue culture. A tissue culture plantlet is typically rooted in 1 to 2 weeks at approximately 25° C.

Root description: Thick, fleshy main roots with fibrous network of much smaller roots. Colored near RHS Yellow-White 158B and Grey-Brown N199A.

PLANT

Age of plant described: Approximately 1 year from a rooted plantlet.

Growth habit: Upright fan shaped perennial with basal only branching.

Pot size: 2 gallon.

Plant type: Compact upright perennial.

Plant habit: Upright growing stems emerge basally.

Plant spread: Approximately 19 cm.

Height:

- *Top of foliar plane.*—20 to 25 cm.
- *Top of flowering plane.*—28 to 35 cm.

Plant spread: 30 to 35 cm.

Growth rate: Moderate.

FOLIAGE

Leaf:

- *Arrangement.*—Basally emerging, irregular rosette. Primarily fan-shaped.
- *Quantity.*—Approximately 35 leaves on a 1 year old plant.
- *Average length.*—Average range 10 to 17 cm.
- *Average width.*—Approximately 1.4 cm (folded).
- *Shape of blade.*—Subulate.
- *Apex.*—Acuminate.
- *Base.*—Clasping.
- *Attachment.*—Sessile.
- *Margin.*—Entire.
- *Texture of top surface.*—Glabrous, scantly hirsute.
- *Texture of lower surface.*—Glabrous, scantly hirsute.
- *Color.*—Young foliage upper side: Near RHS Green 137B. Young foliage under side: Near RHS Green 137B. Mature foliage upper side: Near RHS Green 137A. Mature foliage under side: Near RHS Green 137A.
- *Venation.*—Type: Pinnate. Venation color upper side: Near RHS Green 137A. Venation color under side: Near RHS Green 137A.
- *Petiole.*—Not Present.

FLOWER

Natural flowering season: Freely flowering under outdoors growing conditions with substantially continuous blooming from Spring through Autumn.

Inflorescence and flower type and habit: Primary ramification. Large flowers arranged singly on terminal racemes. Individual flowers are zygomorphic, tubular, with a curved perianth.

Inflorescence height: Approximately 10 to 12 cm.

Inflorescence width: Approximately 6.5 cm.

Flower longevity on plant: Individual flowers last approximately 30 days.

Approximate quantity of flowers per inflorescence: About 8 to 20 flowers and buds per plant.

Persistent or self-cleaning: Persistent.

Bud:

- *Shape.*—Tubular.
- *Length.*—About 2.0 cm.
- *Diameter.*—About 0.5 cm.
- *Texture.*—Pilous.
- *Color.*—Near RHS Yellow 12B background coloration. Heavy pubescence colored near Orange-Red N34A. Apical pubescence colored near Red 53A.

Flower size:

- *Diameter.*—Approximately 3.0 cm (apical section open).
- *Length.*—Approximately 4.5 cm.

Petals (unfused floral section):

- *Length.*—Approximately 1.5 cm.
- *Diameter.*—Approximately 0.4 cm.
- *Quantity.*—6.
- *Texture.*—Exterior covered in dense, pilous hairs. Hairs colored near Orange-Red N34A. Interior glabrous.
- *Apex.*—Acute.
- *Color.*—When opening: Outer, visible surface: Background color near RHS Yellow-Green 144B. Densely colored from pubescence, Red 53A. Fully opened: Outer surface: Background color near RHS Yellow-Green 144B. Densely colored from pubescence, Near Yellow-Orange 22A, apical pubescence near Red 46A. Inner surface: Near RHS Yellow-Green 144A.

Perianth tube:

- *Length.*—Approximately 2.5 cm.
- *Diameter.*—Approximately 0.9 cm.

*Texture*.—Outer texture highly pubescent, inner texture very slightly pubescent.

*Description*.—Flared distally.

*Color*.—When opening: Outer, visible surface: Background color near RHS Yellow-Green 144A. Primary color from pubescence upper surface pubescence colored near Red 53A. Lower surface pubescence colored near Yellow 13C. Fully opened: Outer surface: Background color near RHS Yellow-Green 144C. Primary color from pubescence, Orange 33B. Inner surface: Near RHS Yellow-Green 144B.

Floral bracts:

*Quantity*.—1 at the base of each inflorescence.

*Shape*.—Narrow deltoid.

*Tip*.—Acute.

*Base*.—Clasping.

*Texture*.—Upper surface glabrous, lower surface heavily pilous.

*Length*.—Approximately 2.0 cm.

*Width*.—Approximately 0.5 cm.

*Color*.—Upper surface: Near RHS Yellow-Green 144A. Lower surface: Near RHS Yellow-Green 144A. Covered in hairs near RHS Red 52D.

Peduncle:

*Length*.—Average 8 to 18 cm.

*Diameter*.—0.8 cm.

*Color*.—Near RHS Yellow-Green 144A, covered in hairs colored near Yellow 10D.

*Aspect*.—Straight.

*Strength*.—Very strong.

*Texture*.—Pilous.

Pedicels:

*Length*.—Average 0.2 cm.

*Diameter*.—0.4 cm.

*Color*.—Background color near RHS Yellow-Green 144A. Primary color from pubescence, Yellow 7A.

*Orientation*.—Approximately 45 degrees from peduncle.

*Strength*.—Very strong.

*Texture*.—Pilous.

Sepals not present.

Nectaries not observed.

Fragrance: None.

REPRODUCTIVE ORGANS

Stamens:

*Number*.—5 or 6.

*Filament length*.—Filaments are mostly fused to petals. Approximately 0.7 cm, unfused.

*Filament color*.—Near RHS Yellow-Green 144C.

Anthers:

*Shape*.—Ovoid.

*Length*.—Approximately 0.1 cm.

*Color*.—Near RHS yellow 13A.

*Pollen*.—Not observed.

Pistil:

*Number*.—1.

*Length*.—Approximately 4.0 cm.

*Style*.—Length: Approximately 3.7 cm. Color: Near RHS Yellow-Green 144B.

*Stigma*.—Shape: Linear. Length: Approximately 0.1 cm. Color: Near RHS Yellow-Green 144A. Ovary Color: RHS Yellow-Green 144C.

OTHER CHARACTERISTICS

Seeds and fruits: Not observed to date.

Disease/pest resistance: Neither resistance nor susceptibility to the normal diseases and pests of *Anigozanthos* has been observed.

Temperature tolerance: From approximately 0° C. to more than 40° C.

What is claimed is:

1. A new and distinct cultivar of *Anigozanthos* plant named 'Ramboprise' as herein illustrated and described.

* * * * *